United States Patent [19]

Starks

[11] 3,931,238

[45] Jan. 6, 1976

[54] PREPARATION OF ALCOHOLS AND ETHERS

[75] Inventor: Charles M. Starks, Ponca City, Okla.

[73] Assignee: Continental Oil Company, Ponca City, Okla.

[22] Filed: Apr. 17, 1974

[21] Appl. No.: 461,570

Related U.S. Application Data

[63] Continuation-in-part of Ser. No. 233,714, March 10, 1972, abandoned.

[52] U.S. Cl... 260/346.1 R; 260/611 A; 260/611 B; 260/614 R; 260/615 R; 260/615 B; 260/618 R; 260/639 R; 260/640
[51] Int. Cl.² ............. C07D 307/06; C07C 41/00; C07C 21/00; C07C 29/12
[58] Field of Search ........ 260/346.1, 611, 614, 615, 260/618, 640, 639

*Primary Examiner*—Harry I. Moatz
*Attorney, Agent, or Firm*—Bayless E. Rutherford, Jr.

[57] ABSTRACT

Alcohols and ethers are prepared by reacting a substituted hydrocarbon compound containing halogen or alkyl sulfate groups with an alkali metal hydroxide, in aqueous solution, in the presence of a catalytic amount of certain betaines and recovering from the reaction mixture the desired alcohol and/or ether. The reaction mixture can contain alcohols, ethers, and di-ethers, in varying amounts, depending on reactants and reaction conditions. Typical examples of materials used are: 1,4-dichlorobutane, sodium hydroxide, and tridodecylcarbomethoxymethyl ammonium bromide as the catalyst. The ethers are useful as solvents.

20 Claims, No Drawings

PREPARATION OF ALCOHOLS AND ETHERS

CROSS-REFERENCE TO RELATED APPLICATIONS

The present application is a continuation-in-part of application Ser. No. 233,714, filed Mar. 10, 1972, and now abandoned.

Ser. No. 233,771, entitled "Preparation of Ethers" and wherein the inventor is Ronnie M. Gordon, filed Mar. 10, 1972, and having the same assignee as both Ser. No. 233,714 and the present application, concerns the preparation of symmetrical ethers by the reaction of an organic compound, containing a halogen or alkyl sulfate group with an alkali metal hydroxide, in the presence of a catalytic amount of an organic quaternary salt.

BACKGROUND

Ethers are particularly useful as solvents. Since the boiling points of ethers differ according to the composition, it is desirable to have available ethers of varying compositions in order to meet a variety of boiling point requirements for solvents.

Industrially, symmetrical ethers have been produced by sulfuric acid dehydration of alcohols. Another manner of preparing symmetrical ethers has been by the Williamson synthesis which uses an alkyl halide and a sodium alkoxide (both alkyl groups being the same).

The commonly-assigned application, referred to above, concerns a process for preparing ethers by the reaction of an organic compound, containing a halogen or alkyl sulfate group, with an alkali metal hydroxide, in aqueous solution, in the presence of a catalytic amount of a quaternary salt. I have found that use of certain betaines gives improved results, particularly when higher temperatures are used.

PRIOR ART

From a search of the prior art, the following references are considered to be the most pertinent.

U.S. Pat. No. 2,318,033 teaches the preparation of alcohols by reacting an alkyl halide with an aqueous alkali metal hydroxide in the presence of a salt of a strong base and a weak acid (e.g., the salt of a strong amino base and a weak acid, such as acetic or carbonic acid is suggested). The betaines are not taught in this patent.

U.S. Pat. No. 3,157,705 teaches the preparation of an alcohol by contacting an aliphatic or an alkyl halide, other than a fluoride, with water and an N:N dialkyl amide of a saturated carboxylic acid. The patent states that, if desired, a stronger base can be added to the reaction mixture at the beginning of the process.

U.S. Pat. No. 3,562,315 teaches the preparation of an alcohol and its carboxylic acid ester by the reaction of an organic halide, a carboxylic acid amide, and water at an elevated temperature.

Briefly, it is believed apparent that the references discussed in the foregoing do not suggest the process described herein.

The following additional references were cited in the parent application, either in connection with a restriction requirement or in order to show the state of the art: U.S. Pat. Nos. 711,565; 1,873,538; 1,245,742; 1,873,538; 2,237,241; and 2,818,444.

BRIEF SUMMARY OF THE INVENTION

Broadly stated, my invention is directed to a process for preparing alcohols and ethers by reacting a substituted hydrocarbon compound containing 1 to 40 carbon atoms and containing 1 to 10 halogen atoms, preferably 1 to 3 halogen atoms, which are preferably chlorine or bromine, or an alkyl sulfate group, with an alkali metal hydroxide, in aqueous solution, in the presence of certain betaines and recovering from the reaction mixture the desired alcohol and/or ether.

Depending on reactants and reaction conditions, the reaction mixture contains alcohols, ethers, and diethers. Also, depending on reactants and reaction conditions, the reaction mixture contains substantially all ethers and/or diethers.

Preferably, the substituted hydrocarbon compound is a halogen-substituted hydrocarbon.

An important feature of the process is the use of the betaine as a catalyst. As stated hereinbefore, when higher temperatures are used these materials give improved results.

Other significant features of the process are that it is conducted under autogeneous pressure conditions and does not require the use of an organic solvent.

DETAILED DESCRIPTION

Materials Used and Amounts of Materials Used

Suitable substituted hydrocarbon compounds contain 1 to 40 carbon atoms and contain 1 to 10 halogen atoms, preferably 1 to 3 halogen atoms, which are preferably chlorine or bromine, or an alkyl sulfate group. These substituted hydrocarbon compounds are characterized further in that the hydrocarbon fraction is selected from the group consisting of:

a. terminally substituted linear alkyl groups containing 1 to 18 carbon atoms,
b. 1 to 20 continuous methylene groups,
c. internally substituted alkanes containing 4 to 40 carbon atoms,
d. alkenes containing 3 to 40 carbon atoms, and
e. mono- and di-alkyl substituted monocyclic aromatic compounds containing 7 to 8 carbon atoms.

Examples of suitable substituted hydrocarbon compounds include the following:

a. Primary n-alkyl halides or alkyl sulfates, represented by the formula RZ wherein R is a $C_1$ to $C_{18}$ normal alkyl group and Z is a halogen or an alkyl sulfate group. Preferably, Z is chloride or bromide, and preferably the alkyl moiety of the alkyl sulfate group contains 1 or 2 carbon atoms. Specific examples include methyl chloride, methyl bromide, butyl chloride, butyl bromide, butyl iodide, hexyl chloride, hexyl bromide, octadecyl chloride, octadecyl bromide, methylethylsulfate, butylmethylsulfate, hexylmethylsulfate, octadecylmethylsulfate, and octadecylethylsulfate.

b. Dihaloalkanes represented by the formula $X(CH_2)_nX$ wherein X is a halogen, preferably chlorine or bromine, and $n$ is an integer of 1 to 20. Specific examples include dichloroethane, dibromopropane, dichlorobutane, dichlorooctane, dibromododecane, dichlorohexadecane, dibromooctadecane, and dichloroeicosane.

c. Internally substituted mono-, di-, and polychlorinated or brominated alkanes containing 4 to 40 carbon atoms. Preferably, the chlorinated alkanes are mono- or di-substituted. Specific examples include 2-chlorobutane, 2,4-dichloropentane, 2-chlorohexane, 2,6-dichlorooctane, 2,18-dichloroeicosane, 2,6,18-trichloroeicosane, 2,6,16,18-tetrachloroeicosane, 2,6,8,14,16,18-hexabromoeicosane, 2,4,6,8,10,12,14,16,18-nonachloroeicosene, 2,28-dichlorotriacontane, 2,20,28-trichlorotriacontane, 2,38-dibromotetracontane, 2,38-dichlorotetracontane, 2,20,38-trichlorotetracontane, 2,4,36,38-tetrabromotetracontane, 2,4,6,8,10,12,14,16,18,20-decachlorotetracontane, and 2,4,6,8,10,30,32,34,36,38-decachlorotetracontane.

d. Unsaturated alkyl halides containing 3 to 40 carbon atoms, such a 1-chloro-3-propene, 1,4-dichloro-2-butene, 2,6-dichloro-4-octene, 2,8-dichloro-6-decene, 2,18-dichloro-10-eicosene, 2,18-dibromo-10-eicosene, 2,28-dichloro-20-triacontene, 2,34-dibromo-4-dotriacontene, 4-chloro-1-triacontene, and 2,38-dibromo-10-tetracontene.

e. Mono- and di-chloro-substituted monocyclic aromatic compounds, such as benzyl chloride and α,α'-dichloroxylene.

Of the foregoing materials the chlorinated or brominated hydrocarbons are considered more suitable, with the n-alkyl chlorides or bromides preferred for reasons of economy and availability.

An aqueous solution of alkali metal hydroxide is used. More suitably, the alkali metal is sodium or potassium, but preferably is sodium, for economic reasons. The concentrations of the alkali metal in the water can be in the range of 1 to 70 percent. Preferably, the concentration is not less than 10 percent by weight.

While it is suitable to use stoichiometric amounts of the organic compound and alkali metal hydroxide (i.e., 1:1 mole ratio), preferably an excess of alkali metal hydroxide is used which can be in the range of 2 to 5 times the stoichiometric amount.

Suitable betaines are represented by the following formulae:

(1)   $R'_3M^+(CH_2)_nCO_2R''X^-$ or (2)   $R'_3M^+(CH_2)_nCO_2^-$ wherein
R' is an alkyl group containing from 2 to 20 carbon atoms, but preferably from 4 to 14 carbon atoms, or a mono- or di-alkyl substituted phenyl or benzyl group wherein the alkyl radical contains from 1 to 20 carbon atoms, more suitably from 2 to 20 carbon atoms and preferably from 4 to 14 carbon atoms;
R'' is hydrogen or an alkyl group containing from 1 to 20 carbon atoms, but preferably 1 to 2 carbon atoms;
M is nitrogen or phosphorus;
n is an integer in the range of from 1 to 20, but preferably from 1 to 10; and
X is a halide or alkyl sulfate anion, but preferably is chloride or bromide.

Specific examples of suitable betaines include the following: triethylcarbobutoxyethyl ammonium chloride, tributylcarboeicosoxymethyl ammonium bromide, trihexylcarboproxydecyl ammonium chloride, tridecylcarbomethoxyethyl ammonium methyl sulfate, tridodecylcarbohexoxymethyl ammonium ethyl sulfate, tritetradecylcarbobutyoxyhexyl ammonium bromide, tridodecylcarbomethoxymethyl ammonium bromide, trieicosylcarbomethoxyethyl ammonium chloride, tripropylcarbooctadecoxyethyl ammonium bromide, tributylphenylcarbobutoxyethyl ammonium bromide, trihexylphenylcarbohexoxymethyl ammonium chloride, tridodecylphenylcarbomethoxyethyl ammonium bromide, tributylbenzylcarbobutoxyethyl ammonium bromide, trihexylbenzylcarbohexorymethyl ammonium chloride, tridodecylbenzylcarbomethoxyethyl ammonium bromide, 4-carboxybutyltridodecyl ammonium bromide, 4-carboxyhexyltrioctadecyl ammonium chloride, 4-carboxydecyltridecyl ammonium chloride, 4-carboxyeicosyltrihexyl ammonium bromide, triethylcarbobutoxyethyl phosphonium chloride, tributylcarboeicosoxymethyl phosphonium bromide, trihexylcarboproxydecyl phosphonium chloride, tridecylcarbomethoxyethyl phosphonium methyl sulfate, tridodecylcarbohexoxymethyl phosphonium ethyl sulfate, tritetradecylcarbobutoxyhexyl phosphonium bromide, tridodecylcarbomethoxymethyl phosphonium bromide, trieicosylcarbomethoxyethyl phosphonium chloride, tripropylcarbooctadecoxyethyl phosphonium bromide, tributylphenylcarbobutoxyethyl phosphonium bromide, trihexylphenylcarbohexoxymethyl phosphonium chloride, tridodecylphenylcarbomethoxyethyl phosphonium bromide, tributylbenzylcarbobutoxyethyl phosphonium bromide, trihexylbenzylcarbohexorymethyl phosphonium chloride, tridodecylbenzylcarbomethoxyethyl phosphonium bromide, 4-carboxybutyltridodecyl phosphonium bromide, 4-carboxyhexyltrioctadecyl phosphonium chloride, 4-carboxydecyltridecyl phosphonium chloride, 4-carboxyeicosyltrihexyl phosphonium bromide, and the inner salts of the preceding. (By inner salt is meant materials corresponding to formula (2) in the foregoing.)

Knowing that the betaines described herein are effective as a catalyst in the process of preparing symmetrical ethers described herein, any person skilled in the art can readily determine the optimum amount required. In order to make my disclosure more complete, however, I have found a preferred amount of catalyst to be from about 1 to about 5 percent by weight based on the organic compound. An amount of catalyst as low as 0.01 weight percent is suitable provided a longer reaction time is not undesirable. Similarly, an amount of catalyst as high as 20 weight percent is suitable as long as higher costs are not undesirable.

Process Conditions

The process can be conducted under either batch or continuous operation, but usually is conducted as a batch operation.

The process can be conducted at a temperature in the range of about 25° to about 300°C, preferably in the range of from above 50° to about 150°C. As noted previously when using higher temperatures, e.g., above 50°C, the betaines of my invention give improved results as compared to the other quaternary salts disclosed in related application Ser. No. 233,771.

The reaction time is not critical, being dependent on the particular materials used (e.g., type of organic compound, type of catalyst, and concentration of catalyst and/or alkali metal hydroxide).

No solvent is required other than the water for making an aqueous alkali metal hydroxide solution.

The reaction is conducted under autogeneous pressure; in other words, the only pressure is that which is self-generated by the materials and process conditions. It is not necessary to use intentionally created conditions in order to produce a higher pressure in the reaction system.

In order to show the products obtained by my process, the reactions which occur are shown below, using an alkyl chloride as the organic compound:

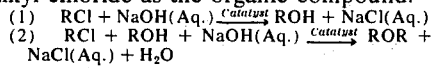

Since the reaction kinetics favor the second reaction, a major amount of ether is formed in the reaction mixture.

In addition the following reaction may occur:

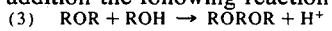

It is to be understood that the reactions shown in the foregoing are merely illustrative and are not intended to limit my invention. For example, my process can also be used to prepare unsymmetrical ethers and unsymmetrical diethers.

The combined reaction product, alcohol and ether, and possibly diether, can be recovered from the reaction mixture as one product. Also, if desired, by careful distillation conditions, the individual products can be recovered from the reaction mixture. The alcohol recovered from the reaction mixture can be recycled to the process to increase the yield of ether, if desired.

In order to disclose the nature of the present invention more specifically, the following illustrative examples will be given. It is to be understood that the invention is not to be limited to the specific conditions or details set forth in these examples except insofar as these limitations are specified in the appended claims.

EXAMPLE 1

This example illustrates the effect of various quaternary salts, including betaines, in the reaction of 1,4-dibromobutane with aqueous sodium hydroxide.

A mixture of 1,4-dibromobutane (30 ml); tridecane used as in internal GLC (gas liquid chromatography) standard (15 ml); catalyst, 2.0 g; and 100 ml of 50 percent aqueous sodium hydroxide was heated to 75°C with constant speed stirring at 500 rpm. Samples of the organic phase were periodically removed for analysis. From these data rate constants for the disappearance of 1,4-dibromobutane and for the formation of tetrahydrofuran were calculated:

| Catalyst | Rate Constant (Min$^{-1}$) at 75°C × 10$^4$ |
|---|---|
| None | No detectable reaction |
| $(C_{12}H_{25})_3$ N | 1.7 |
| $(C_{12}H_{25})_3$ N$^+$C$_4$H$_9$ Br$^-$ | 3.0 |
| $(C_{12}H_{25})_3$ N$^+$CH$_2$CH$_2$CO$_2$H Br$^-$ | 9.7 |
| $(C_{12}H_{25})_3$ N$^+$CH$_2$CO$_2$H Br$^-$ | 86 |
| $(C_{12}H_{25})_3$ N$^+$(CH$_2$)$_7$ CO$_2$H Br$^-$ | 51 |
| $(C_{16}H_{33})_2$ N$^+$(C$_6$H$_{13}$)$_2$ Br$^-$ | 2.1 |

The data represented above shows that the betaines are superior catalysts for ether formation at higher temperatures, such as 75°C.

EXAMPLE 2

A mixture of 30 ml 1,4-dichlorobutane, 50 ml of 50 percent aqueous sodium hydroxide, and 2 g of $(C_{12}H_{25})_3$ N$^+$ CH$_2$CO$_2$CH$_3$ Br$^-$ was stirred at 50°C for 36 hours. Analysis of the organic phase of the reaction mixture showed it to contain 66.7 weight percent tetrahydrofuran, 33.3 weight percent 1,4-dichlorobutane, and ca 1.0 percent of all other impurities.

EXAMPLE 3

A mixture of 10 ml ethylene glycol, 25 ml of 1-bromooctane, and 25 ml of 50 percent sodium hydroxide solution was mixed with 1 g $(C_{12}H_{25})_3$ N$^+$ CH$_2$CO$_2$CH$_3$ Br$^-$ and heated with stirring at 60°–80°C for 48 hours. Analysis of the organic phase showed it to contain 9.1 percent ethylene glycol, 6.3 percent 1-octanol, 3.3 percent 1-bromooctane, 5.4 percent $C_8H_{17}O$—$CH_2CH_2OH$, 20.9 percent $(C_8H_{17})_2$ O, and 54.0 percent $C_8H_{17}O$—$CH_2CH_2O$—$C_8H_{17}$.

EXAMPLE 4

A mixture of 5.0 g 1-bromooctane, 6.1 g tridecane, 1.5 g $(C_{12}H_{25})_3$ N$^+$ CH$_2$CO$_2$CH$_3$ Br$^-$, and 15 ml of aqueous 50 percent sodium hydroxide was heated with stirring at 90°C for 24 hours. Analysis of the organic phase showed that 76 percent of the 1-bromooctane had been converted to a mixture of octanol and dioctyl ether.

Having thus described the invention by providing specific examples thereof, it is to be understood that no undue limitations or restrictions are to be drawn by reason thereof and that many variations and modifications are within the scope of the invention.

The invention having thus been described, what is claimed and desired to be secure by Letters Patent is:

1. A process for preparing alcohols and ethers wherein the process comprises reacting a substituted hydrocarbon compound containing 1 to 40 carbon atoms and containing 1 to 10 chlorine or bromine atoms or an alkyl sulfate group, with at least a stoichiometric amount of an alkali metal hydroxide, in aqueous solution, at a temperature in the range of about 25° to about 300°C in the presence of a catalytic amount, in the range of from about 0.01 to about to about 20 weight percent based on said organic compound, of a betaine, and recovering from the reaction mixture by distillation said alcohol and said ether, said process being characterized further in that:

A. the hydrocarbon fraction of the substituted hydrocarbon compound is selected from the group consisting of:
  1. terminally substituted linear alkyl groups containing 1 to 18 carbon atoms,
  2. 1 to 20 continuous methylene groups,
  3. internally substituted alkanes containing 4 to 40 carbon atoms,
  4. alkenes containing 3 to 40 carbon atoms, and
  5. mono- and di-haloakyl-substituted monocyclic aromatic compounds selected from the group consisting of benzyl chloride and α,α'-dichloroxylene, and B. the betaine is selected from the group consisting of:
  1. compounds represented by the formula
     R'$_3$M$^+$(CH$_2$)$_n$CO$_2$R''X$^-$, and
  2. compounds represented by the formula
     R'$_3$M$^+$(CH$_2$)$_n$CO$_2^-$
  wherein
     R' is selected from the group consisting of alkyl groups containing from 2 to 20 carbon atoms and mono- or di-alkyl substituted phenyl or benzyl groups, wherein the alkyl radical contains from 1 to 20 carbon atoms, R'' is selected from the group consisting of hydrogen and alkyl groups containing from 1 to 20 carbon atoms, M is selected from the group consisting of nitrogen and phosphorus, n is an integer in the range of 1 to 20, and x is selected from the group consisting of halides and alkyl sulfates.

2. The process of claim 1 wherein the amount of catalyst is from about 1 to about 5 weight percent based on said substituted hydrocarbon compound.

3. The process of claim 2 wherein the alkali metal hydroxide is sodium hydroxide and the amount of alkali metal hydroxide, based on said substituted hydrocarbon on a molar basis, is in the range of about 2:1 to about 5:1.

4. The process of claim 3 wherein the temperature is in the range of from above 50° to about 150°C.

5. The process of claim 4 wherein the substituted hydrocarbon compound is a primary n-alkyl halide or alkyl sulfate represented by the formula RZ wherein R is a $C_1$ to $C_{18}$ normal alkyl group and Z is a halide or alkyl sulfate anion.

6. The process of claim 4 wherein the substituted hydrocarbon compound is a dihaloalkane represented by the formula $X(CH_2)_nX$ wherein X is chlorine or bromine and n is an integer of 1 to 20.

7. The process of claim 4 wherein the substituted hydrocarbon compound is an internally substituted mono-, di-, or tri-chlorinated or brominated alkane containing 4 to 40 carbon atoms.

8. The process of claim 4 wherein the substituted hydrocarbon compound is an alkene containing 3 to 40 carbon atoms and 1 to 2 chlorine or bromine atoms.

9. The process of claim 4 wherein the substituted hydrocarbon compound is a mono- or di-chloro alkyl substituted aromatic compound selected from the group consisting of benzyl chloride and $\alpha,\alpha'$-dichloroxylene.

10. A process for preparing ethers wherein the process comprises reacting a halogen substituted hydrocarbon, containing 1 to 40 carbon atoms, wherein the halogen is bromine or chlorine, with at least a stoichiometric amount of sodium hydroxide, in aqueous solution, at a temperature in the range of from above 50° to about 150°C, in the presence of a catalytic amount, in the range of from about 0.01 to about 20 weight percent, of a betaine and recovering from the reaction mixture by distillation the desired ether, said process being characterized further in that:

A. the hydrocarbon fraction of the substituted hydrocarbon compound is selected from the group consisting of:
1. terminally substituted linear alkyl groups containing 1 to 18 carbon atoms,
2. 1 to 20 continuous methylene groups,
3. internally substituted alkanes containing 4 to 40 carbon atoms,
4. alkenes containing 3 to 40 carbon atoms, and B. the betaine is selected from the group consisting of:
1. compounds represented by the formula
$R'_3M^+(CH_2)_nCO_2R''X^-$, and
2. compounds represented by the formula
$R'_3M^+(CH_2)_nCO_2^-$
wherein
R' is selected from the group consisting of alkyl groups containing from 2 to 20 carbon atoms and mono- or di-alkyl substituted phenyl or benzyl groups, wherein the alkyl radical contains from 1 to 20 carbon atoms,
R'' is selected from the group consisting of hydrogen and alkyl groups containing from 1 to 20 carbon atoms,
M is selected from the group consisting of nitrogen and phosphorus,
n is an integer in the range of 1 to 20, and
X is selected from the group consisting of halides and alkyl sulfates.

11. The process of claim 10 wherein in the betaine catalyst M is nitrogen and X is a halide anion which is chloride or bromide.

12. The process of claim 11 wherein the sodium hydroxide is present in an amount of from about 2 to about 5 moles per mole of halogen-substituted hydrocarbon and the amount of betaine catalyst is from about 1 to about 5 weight percent based on the halogen-substituted hydrocarbon.

13. The process of claim 12 wherein the halogen-substituted hydrocarbon is an n-alkyl halide, wherein the halogen is chlorine or bromine, containing from 1 to 18 carbon atoms.

14. The process of claim 12 wherein the halogen-substituted hydrocarbon is an internally substituted mono-, di-, or tri-chlorinated or brominated alkane containing 4 to 40 carbon atoms.

15. The process of claim 12 wherein the halogen-substituted hydrocarbon is an alkene containing 3 to 40 carbon atoms and 1 to 2 chlorine or bromine atoms.

16. The process of claim 10 wherein in the betaine catalyst M is phosphorus and X is a halide anion, which is chloride or bromide.

17. The process of claim 16 wherein the sodium hydroxide is present in an amount of from about 2 to about 5 moles per mole or halogen-substituted hydrocarbon and the amount of betaine catalyst is from about 1 to about 5 weight percent based on the halogen-substituted hydrocarbon.

18. The process of claim 17 wherein the halogen-substituted hydrocarbon is an n-alkyl halide, wherein the halogen is chlorine or bromine, containing from 1 to 18 carbon atoms.

19. The process of claim 17 wherein the halogen-substituted hydrocarbon is an internally substituted mono-, di-, or tri-chlorinated or brominated alkane containing 4 to 40 carbon atoms.

20. The process of claim 17 wherein the halogen-substituted hydrocarbon is an alkene containing 3 to 40 carbon atoms and 1 to 2 chlorine or bromine atoms.

* * * * *